(12) United States Patent
Shigematsu et al.

(10) Patent No.: US 7,488,405 B2
(45) Date of Patent: Feb. 10, 2009

(54) ELECTRODE FOR ELECTROCHEMICAL MEASUREMENT AND METHOD FOR MANUFACTURING THE SAME

(75) Inventors: Taishi Shigematsu, Ashigarakami-gun (JP); Miho Watanabe, Ashigarakami-gun (JP); Chikara Manabe, Ashigarakami-gun (JP); Hiroyuki Watanabe, Ashigarakami-gun (JP)

(73) Assignee: Fuji Xerox Co., Ltd., Tokyo (JP)

( * ) Notice: Subject to any disclaimer, the term of this patent is extended or adjusted under 35 U.S.C. 154(b) by 934 days.

(21) Appl. No.: 10/866,725

(22) Filed: Jun. 15, 2004

(65) Prior Publication Data

US 2005/0129939 A1  Jun. 16, 2005

(30) Foreign Application Priority Data

Dec. 15, 2003   (JP)  ............................ 2003-417036

(51) Int. Cl.
*G01N 27/00* (2006.01)
(52) U.S. Cl. ..................... 204/400; 977/742; 977/745; 977/748; 977/932; 977/948
(58) Field of Classification Search ............... 977/742, 977/745, 748, 932, 948; 204/400
See application file for complete search history.

(56) References Cited

U.S. PATENT DOCUMENTS

| | | | |
|---|---|---|---|
| 5,900,453 A * | 5/1999 | Egami et al. ................. 524/514 |
| 6,066,448 A | 5/2000 | Wohlstadter et al. |
| 6,090,545 A | 7/2000 | Wohlstadter et al. |
| 6,391,932 B1 * | 5/2002 | Gore et al. ..................... 521/61 |
| 6,821,562 B2 * | 11/2004 | Demaray et al. ......... 427/248.1 |
| 2002/0046872 A1 * | 4/2002 | Smalley et al. ........... 174/137 A |
| 2003/0181560 A1 * | 9/2003 | Kawaguchi et al. ......... 524/424 |
| 2005/0116861 A1 * | 6/2005 | Anazawa et al. ...... 343/700 MS |
| 2006/0138394 A1 | 6/2006 | Den et al. |

FOREIGN PATENT DOCUMENTS

| | | |
|---|---|---|
| JP | A 3-272449 | 12/1991 |
| JP | A-2003-109689 | 4/2003 |
| JP | A 2003-227808 | 8/2003 |
| WO | WO 03/038837 A1 | 5/2003 |

OTHER PUBLICATIONS

Stanley Pons et al.; "The Behavior of Microelectrodes"; Analytical Chemistry, vol. 59, No. 24; Dec. 15, 1987; pp. 1391A-1399A.
Celestino Padeste et al.; "Ferrocene-avidin conjugates for bioelectrochemical applications"; Biosensors & Bioelectronics 15; 2000; pp. 431-438.

* cited by examiner

*Primary Examiner*—Alexa Neckel
*Assistant Examiner*—Zulmariam Mendez
(74) *Attorney, Agent, or Firm*—Oliff & Berridge, PLC

(57) ABSTRACT

The present invention provides an electrode for electrochemical measurement including: a carbon nanotube and an insulator that encloses carbon nanotube, wherein: the carbon nanotube is enclosed by being chemically bonded with the insulator; and part of the carbon nanotube forms an electrical conduction part exposed at a surface of the insulator. The carbon nanotube can include plural carbon nanotubes electrically connected with each other. The electrical conduction part can be part of the plural carbon nanotubes exposed in plural spots at a surface of the insulator through the insulator. The plural carbon nanotubes can form a network structure by being electrically connected with each other by chemical bonding. The present invention also provides a method for manufacturing the electrode for electrochemical measurement.

6 Claims, 6 Drawing Sheets

ELECTRODE FOR ELECTROCHEMICAL MEASUREMENT AND METHOD FOR MANUFACTURING THE SAME

CROSS-REFERENCE TO RELATED APPLICATIONS

This application claims benefit of and priority to Japanese Patent Application No. 2003-417036, which is incorporated herein by reference in its entirety for all purposes.

BACKGROUND OF THE INVENTION

1. Field of the Invention

The present invention relates to an electrode for electrochemical measurement used in sensors for detecting specific substances, and a method for manufacturing the same.

2. Description of the Related Art

Conventionally, attempts have been made to use carbon nanotubes in electronic devices because of their semiconductive characteristics.

The advantage of using carbon nanotubes as electronic devices is their extremely high conductivity. Their small diameters of 1 to 20 nm or so make them suitable for use as devices and electrodes in micro circuits.

On the other hand, from the viewpoint of application to the medical field, biosensors for detecting trace amounts of biological substances are being heavily studied and developed. Detecting methods in actual use can be classified into three methods: (1) an electrochemical method, (2) an enzymatic method, and (3) an staining method.

Of these, the electrochemical method is the most general detecting method. Substances have oxidation-reduction potentials unique thereto, and by applying a specific potential, electrons can be pulled out of (oxidation) or injected into (reduction) a substance. Therefore, the electron exchanges involved in the oxidation-reduction reactions can be measured by cyclic voltammetry or the like so as to find the amount of the target substance from the current value at a certain potential.

In the electrochemical method, micro electrodes are used to improve detecting sensitivity. The micro electrodes refer to electrodes having sizes of a micrometer level or smaller, while the electrodes generally used for electrochemical measurement have sizes of several millimeters to several centimeters (see, for example, S. Pons and M. Fleishmann, Analytical Chemistry, 1987, volume 59, page 1391A). The use of such micro electrodes has the following features (1) to (4).
(1) The provision of charging current which is noise can be reduced.
(2) Potential can be scanned at a high speed.
(3) The effects of substance dispersion can be reduced.
(4) High sensitivity measurement can be accomplished.

Due to these features, the use of micro electrodes is becoming the mainstream in detecting trace amounts of samples by the electrochemical method.

However, metal electrodes such as platinum and gold and carbon electrodes which are generally used in the electrochemical method have a narrow potential window, which causes a problem in that applying a potential higher than a certain level electrolyzes not only the target substance but also the solvent itself, hindering detection of the target substance. This requires using different electrodes depending on the potential to be used, making it impossible to measure cyclic voltammetries at the same time with a wide potential. In recent years, as an electrode with a wide potential window capable of solving this problem, an electrode containing boron-doped diamond has been developed. However, it has not been put into practical use as a general-purpose product because of its high cost.

On the other hand, the enzymatic method is a method for detecting a target substance electrochemically by using an electrode having an enzyme fixed on its surface. Enzymes have the feature of being capable of selectively detecting a target substance at comparatively high sensitivity from a mixture because they react uniquely with the target substance. So far, glucose sensors (diabetes testing), uric acid sensors (gout testing), and urea sensors (kidney function testing) are already in actual use in the medical field. However, there is a problem in that enzymes are difficult to handle because they are unstable and must be stored under special conditions to maintain their activity.

The staining method is a method for detecting a biological substance by measuring the ultraviolet-visible absorption spectrum using a reagent which is colored in a reaction with the target substance, and by finding its absorbance. However, the detecting sensitivity in the absorbance measurement is proportional to the light path length, so that to improve the sensitivity requires a large amount of sample solution. Thus, there is a problem in that the method cannot be applied for the detection of trace amounts of samples.

Specific examples of sensors utilizing the electrochemical detecting method include: sensors for detecting a specific substance by using ion sensitive field-effect transistors (see, for example, Japanese Patent Application Laid-open (JP-A) No. 03-272449); sensors for detecting hydrogen peroxides by using an electrode with ferrocene fixed on its surface (see, for example, C. Padeste et. al, "Ferrocene-avidin conjugates for bioelelectrochemical applications," Biosensors & Bioelectronics, 2000, volume 15, pp. 431-8); and sensors for detecting a specific substance by using a carbon nanotube as an electrode and making use of changes in electrical properties of the carbon nanotube due to external stimulation (See, for example, JP-A No. 2003-227808). However, these sensors are unsatisfactory in terms of the aforementioned viewpoint, and improvements are still expected.

SUMMARY OF THE INVENTION

The present invention provides an electrode for electrochemical measurement which can detect trace amounts of substance, and a method for manufacturing the electrode.

In other words, the first aspect of the invention is an electrode for electrochemical measurement comprising a carbon nanotube and an insulator that encloses carbon nanotube, wherein: the carbon nanotube is enclosed by being chemically bonded with the insulator; and part of the carbon nanotube forms an electrical conduction part exposed at a surface of the insulator.

The second aspect of the invention is a method for manufacturing an electrode for electrochemical measurement, comprising a polymerization reaction in a mixed solution of a polyhydric alcohol and a carbon nanotube modified with a functional group which causes a polymerization reaction with the polyhydric alcohol in the presence of a polymerization catalyst.

BRIEF DESCRIPTION OF THE DRAWINGS

Preferable embodiments of the present invention will be described in detail based on the following figures.

DETAILED DESCRIPTION OF THE INVENTION

The present invention will be described as follows with reference to the drawings. The components having substantially the same functions will be referred to with the same reference symbols throughout the drawings.

First Embodiment

Figure 1A:
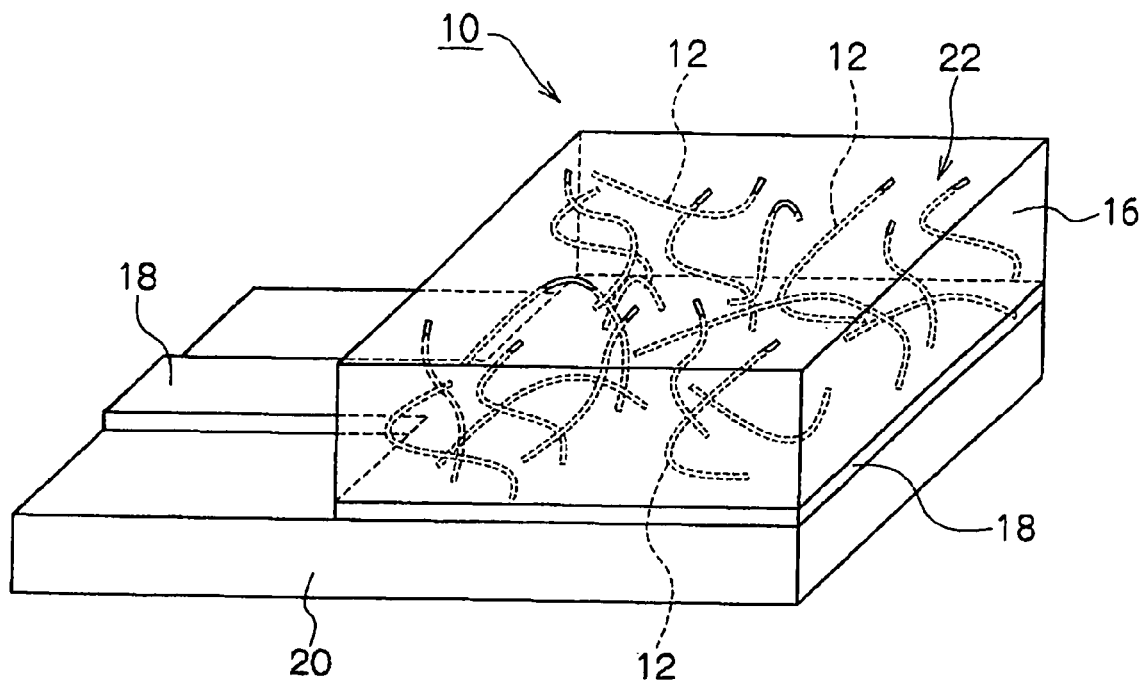
FIG. 1A is a plan view of a simplified structure of an electrode for electromechanical measurement according to a first embodiment of the invention.
Figure 1B:
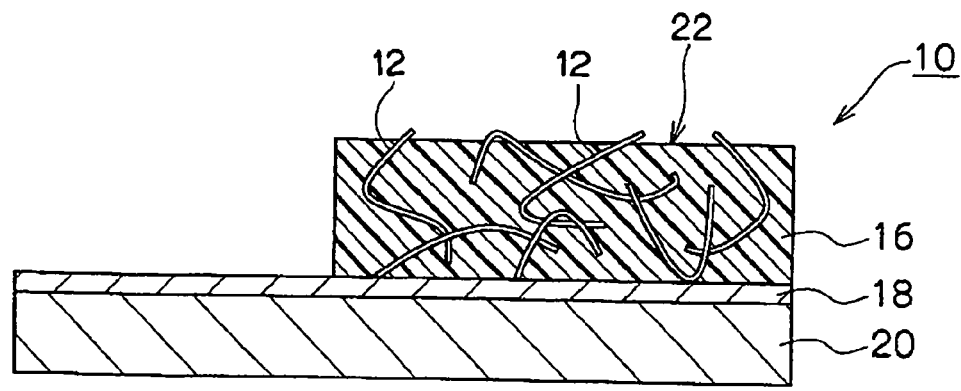
FIG. 1B is a cross sectional view of the structure.

FIG. 1 is a simplified structural view showing the electrode for electromechanical measurement according to the first embodiment of the invention; 1A is a plan view, and 1B is a cross sectional view.

The electrode 10 for electrochemical measurement of the present embodiment comprises an insulator 16 into which plural carbon nanotubes 12 have been enclosed, and the electrode 10 is provided on the substrate 20 having a conductor 18 for current extraction. The plural carbon nanotubes 12 are enclosed in the insulator 16 in such a manner as to be chemically bonded with the insulator 16 and to be electrically connected with each other. The substrate 20 is not an essential component; the insulator 16 could be provided as an electrode, for example, on a film-like conductor 18 for current extraction.

Parts of the plural carbon nanotubes 12 are exposed at a surface of the insulator 16 through the insulator 16 so as to form an electrical conduction part 22. In other words, the plural carbon nanotubes 12 are exposed in plural spots in a mutually electrically isolated condition. Consequently, the exposed carbon nanotubes 12 act as an electrode part, the carbon nanotubes 12 enclosed into the insulator 16 act as conducting wires, and the insulator 16 acts as an insulating film. The conductor 18 for current extraction is electrically connected with parts of the plural carbon nanotubes 12.

In the electrical conduction part 22, the carbon nanotubes 12 exposed in plural spots are electrically conducted in parallel, and current is extracted into the conductor 18 for current extraction through the carbon nanotubes 12 electrically connected with each other in the insulator 16.

Since the plural carbon nanotubes 12 are enclosed in the insulator 16 in a mutually electrically connected condition, the current detected in the electrical conduction part 22 is extracted into the conductor 18 for current extraction with almost no loss.

The electrode for electrochemical measurement can be of any shape such as a rectangular parallelepiped, a cylinder, or the like.

In the electrode for electrochemical measurement of the present embodiment, the carbon nanotubes 12 with extremely high conductive efficiency are enclosed into the insulator 16 in the state of being chemically bonded with the insulator 16, so that the degree of bonding between the carbon nanotubes 12 and the insulator 16 is high, making it harder for the carbon nanotubes 12 to fluctuate inside the insulator 16. This enables the detection of trace amounts of substance, and also broadens the potential window when liquid is measured. Furthermore, the electrode, which comprises the carbon nanotubes 12 and the insulator 16, can be handled in a stable manner in the air.

The potential window to obtain the electrode for electrochemical measurement of the present embodiment is preferably in a range of 4 to 8 V, more preferably in a range of 5 to 8 V, and further preferably in a range of 6 to 8 V. In these ranges, it is possible to measure cyclic voltammetries at the same time in a wide potential, causing the electrolysis of the target substance only, without causing the electrolysis of the solvent itself.

In the electric conductive part 22, the carbon nanotubes 12 exposed in plural spots are conducted in parallel, which can improve the detecting sensitivity.

In the present embodiment, plural carbon nanotubes are used to establish parallel electric connection; however, it is possible to use a single carbon nanotube to compose an electrode. In that case, part of the single carbon nanotube is exclusively exposed at a surface of the insulator so as to make the substantial electrode part micro-sized, thereby accomplishing a high-sensitive sensor, when it is used as a sensor.

Second Embodiment

Figure 2A:
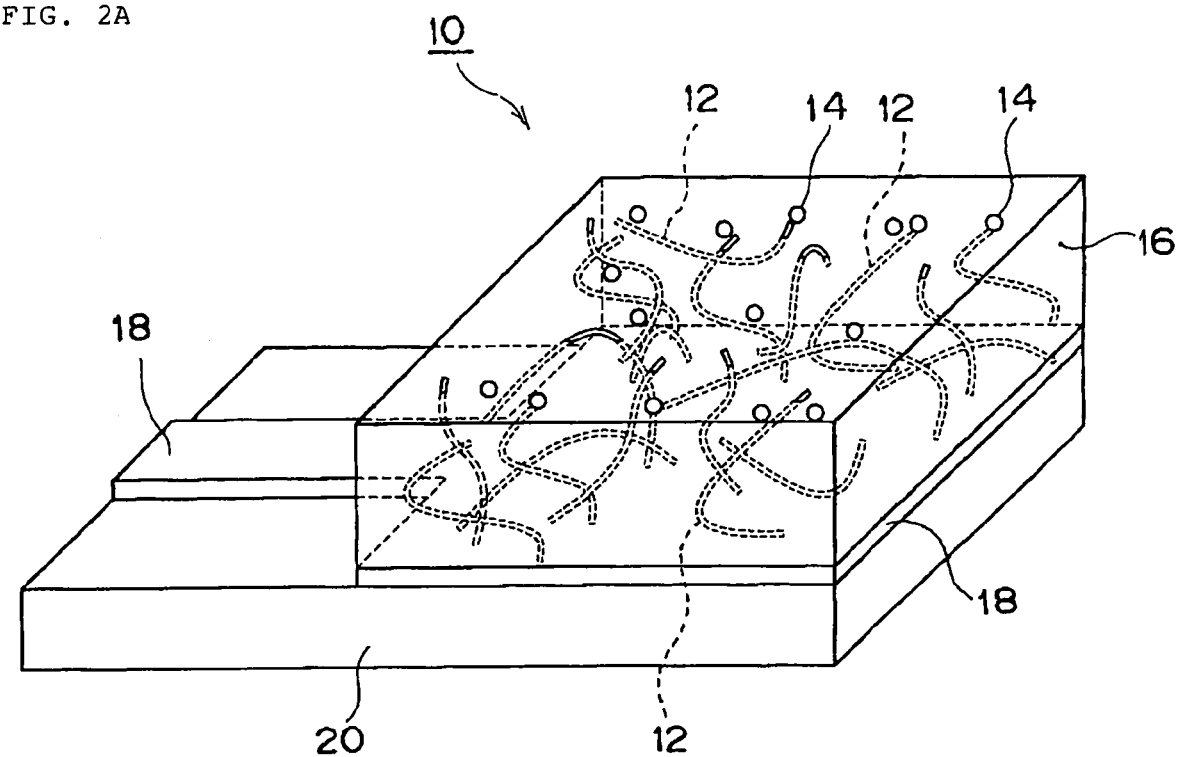
FIG. 2A is a plan view of a simplified structure of an electrode for electromechanical measurement according to a second embodiment of the invention.
Figure 2B:
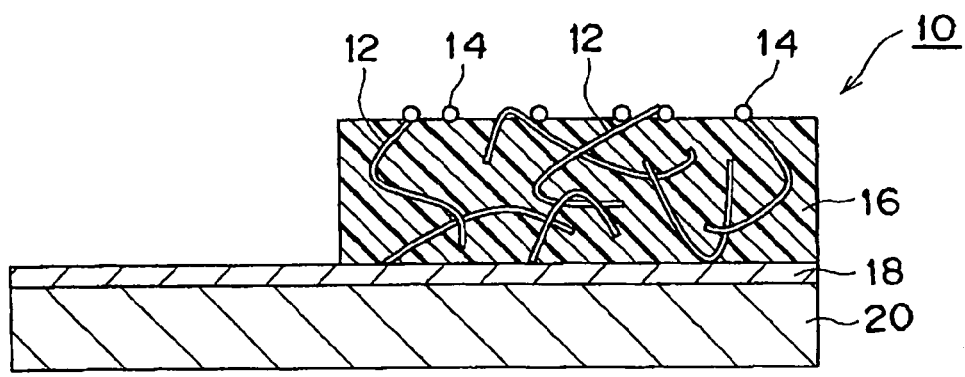
FIG. 2B is a cross sectional view of the structure.

FIG. 2 shows a simplified structure of the electrode for electromechanical measurement according to the second embodiment of the invention; 2A is a plan view, and 2B is a cross sectional view.

The electrode 10 for electrochemical measurement of the present embodiment comprises the insulator 16 into which a catalyst 14 for measurement causing a specific chemical reaction is further enclosed. In this embodiment, the catalyst 14 is exposed at a surface of the insulator 16, and parts of the plural carbon nanotubes 12 are also exposed at a surface of the insulator 16 in a mutually electrically isolated condition by the insulator 16 so as to form the electrical conduction part 22. Consequently, the catalyst 14 for measurement acts as an electrode part (chemical reaction part), the carbon nanotubes 12 act as conducting wires, and the insulator 16 acts as an insulating film. The other structure is identical to the first embodiment, and its description will be omitted.

Figure 3:
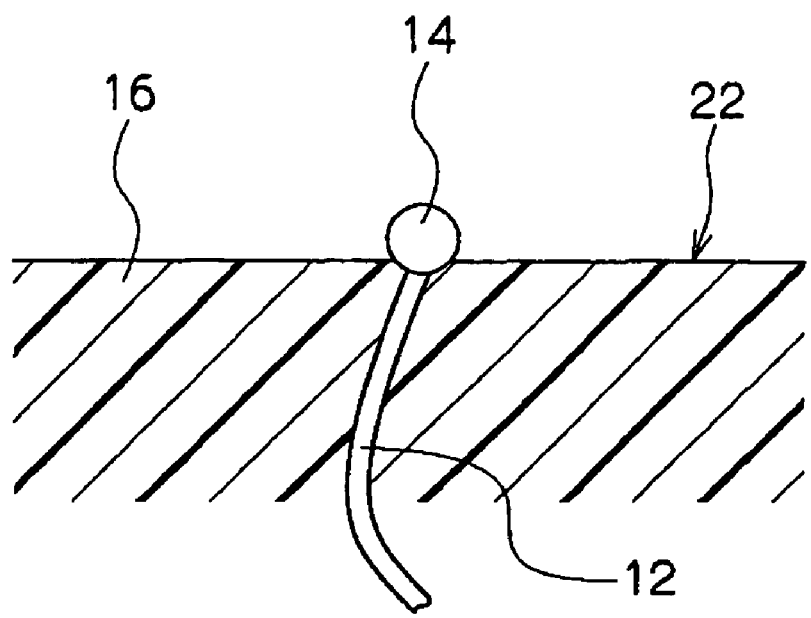
FIG. 3 is a simplified cross sectional view showing a portion of the electrical conduction part of the electrode for electrochemical measurement according to the second embodiment of the invention.
Figure 4:
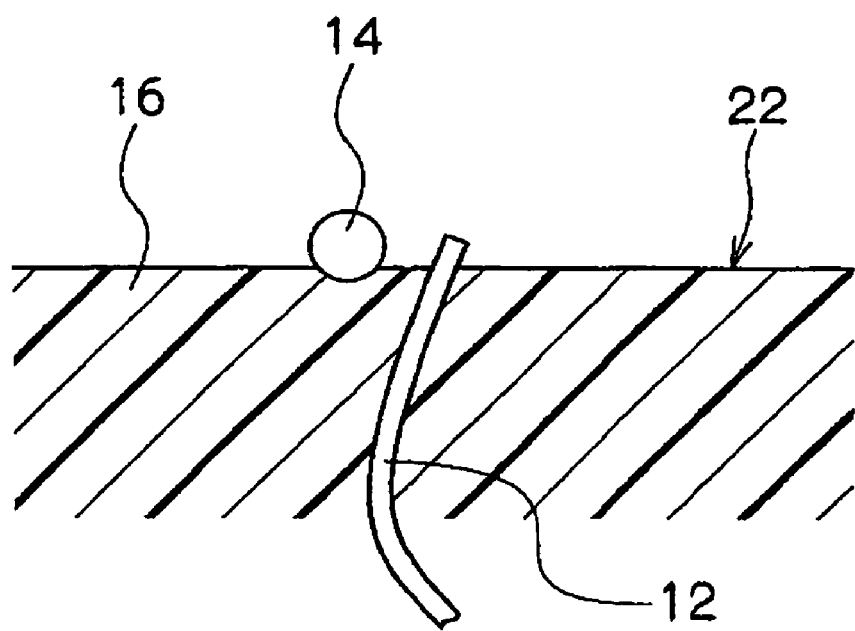
FIG. 4 is another simplified cross sectional view showing a portion of the electrical conduction part of the electrode for electrochemical measurement according to the second embodiment of the invention.

The conduction part 22 has two conditions in mixture: a first condition is that as shown in FIG. 3, parts of the carbon nanotubes 12 are electrically connected with the catalyst 14 for measurement exposed at a surface of the insulator 16, and the second condition is that as shown in FIG. 4, the catalyst 14 for measurement and the carbon nanotubes 12 are independently exposed at a surface of the insulator 16. Although the electrical conduction part 22 shown is in the mixture of the first and second conditions, it has either one of the conditions.

In the first condition, the movements of electrons involved in the chemical reaction caused by the catalyst 14 for measurement are detected by the carbon nanotubes 12 directly connected with the catalyst 14 for measurement. On the other hand, in the second condition, the movements of electrons involved in the chemical reaction caused by the catalyst 14 for measurement are detected by the carbon nanotubes 12 exposed in the vicinity of the catalyst 14 for measurement.

In either condition, the carbon nanotubes 12 detect in parallel the movements of electrons involved in the chemical reaction caused by the catalyst 14 for measurement at plural spots in the electrical conduction part 22, and current is extracted into the conductor 18 for current extraction through the carbon nanotubes 12 electrically connected with each other in the insulator 16.

The chemical reaction caused by the catalyst 14 for measurement functioning as the electrode part is thus detected by the carbon nanotubes 12 with excellent conductive efficiency, which makes it possible to improve the detecting sensitivity more effectively.

Furthermore, the chemical reaction caused by the catalyst 14 for measurement functioning as the electrode part is detected in plural spots in parallel by the carbon nanotubes 12, which can improve the detecting sensitivity.

In general, the substance detection by the electrochemical method has the feature of increasing the sensitivity with decreasing electrode size, so that the detecting sensitivity can be improved by reducing the size of the catalyst 14 for measurement functioning as the electrode part.

The aforementioned materials will be described in detail as follows. Reference symbols will be omitted.

Carbon Nanotubes

The carbon nanotubes can be either single-walled carbon nanotubes or multi-walled carbon nanotubes. Which carbon nanotubes should be used or whether both are mixed or not can be selected appropriately. It is also possible to use as the carbon nanotubes those not exactly tube-shaped such as a carbon nano horn which is a variation of the single-walled carbon nanotube (a horn type whose diameter is continuously enlarged from one end to the other), a carbon nano coil (a coil type having a spiral shape as a whole), a carbon nano bead (a type having a tube in the center and the tube penetrates a spherical bead composed of amorphous carbon or the like), a cup stacked type, or a carbon nanotube coated with a carbon nano horn or amorphous carbon.

There are other kinds of tubes which can be used as the carbon nanotubes, such as metal-containing nanotubes containing metal or the like, peapod nanotubes containing fullerene or metal-containing fullerene, and other carbon nanotubes containing any substance.

As described hereinbefore, besides general carbon nanotubes, the invention can use any types of carbon nanotubes including those variously modified, without any problem when viewed from their reactivity. Therefore, the "carbon nanotube" in the invention includes all of these in its concept.

In the case that the carbon nanotubes are electrically connected with each other by the mutual contact, the bending of the electrode and other operations can change the contact condition, fluctuating mechanical and electric strength, thereby failing to fully exert the performance. In addition, to increase the electric conductivity requires to increase the amount of carbon nanotubes to be filled (to be enclosed), which might decrease the amount of the insulator, thereby decreasing the mechanical strength of the electrode itself.

Therefore, the carbon nanotubes preferably form a network structure by being electrically connected with each other by chemical bonding, from the viewpoint of improving the electric conductivity and mechanical strength of the carbon nanotubes themselves and the electrode intensity. One specific example is a cross-linked carbon nanotube structure in which the functional groups bonded with plural carbon nanotubes are chemically bonded with each other to form a network structure.

The cross-linked carbon nanotube structure has cross-linked positions formed by chemically bonding the functional groups of the plural carbon nanotubes. The cross-linked positions can preferably have either a first structure in which plural functional groups are cross-linked with each other by using a cross-linking agent, or a second structure in which plural functional groups are bonded chemically with each other.

The first structure is a cross-linked structure where functional groups remain after the cross-linking reaction are linked with each other by linking groups of the cross-linking agent which remain after the cross-linking reaction.

When the cross-linking agent has the property of causing a polymerization reaction in it (self polymerization), the structure might fall into the condition of containing a polymer consisting of two or more linked groups of the cross-linking agent as linking groups, which decreases the substantial density of the carbon nanotubes in the cross-linked carbon nanotube structure. The result is insufficient electric conductivity or mechanical strength of the electrode.

On the other hand, when the cross-linking agent has the property of non-self-polymerization, the spacing between the carbon nanotubes can be controlled to meet the size of the remaining groups of the used cross-linking agent, so that a desired carbon nanotube network structure can be acquired at high reproducibility. Furthermore, a reduction in the size of the remaining groups of the cross-linking agent enables the spacing between the carbon nanotubes to be in the condition that the carbon nanotubes are extremely close to each other both electrically and physically. In addition, the carbon nanotubes can be densely formed in the structure.

Therefore, if the cross-linking agent has the property of non-self-polymerization, the cross-linked carbon nanotube structure can be allowed to exert the electric properties or mechanical strength of the carbon nanotubes themselves at a high order. In the invention, the property of "self polymerization" indicates that the cross-linking agent groups can cause a polymerization reaction in the presence of water and other ingredients or in the absence of other ingredients, while the "non-self-polymerization" indicates the absence of such property.

Here, if a cross-linking agent with the property of non-self-polymerization is selected, the cross-linked positions where the carbon nanotubes are cross-linked with each other mainly form the same cross-linked structure. The linking groups preferably have a hydrocarbon as a skeleton, and preferably have 2 to 10 carbons. Decreasing the number of carbons can shrink the length of the cross-linked positions so as to arrange the carbon nanotubes close enough to each other in comparison with the lengths of the carbon nanotubes themselves, thereby accomplishing a cross-linked carbon nanotube structure with a network structure composed of carbon nanotubes substantially exclusively.

In the first structure, examples of the functional group include: —OH, —COOH, —COOR (R is a substituted or unsubstituted hydrocarbon group), —COX (X is a halogen atom), —NH$_2$, and —NCO, and it is preferable to select at least one group selected from these. In that case, a substance which can cause a cross-linking reaction with the selected functional group can be selected as the cross-linking agent.

Preferable cross-linking agents include: polyols, polyamines, polycarboxylic acids, polycarboxylic esters, polycarboxylic halides, polycarbodiimides, and polyisocyanates. It is preferable to select at least one cross-linking agent from the group consisting of these, and in that case, a substance which can be cross-linked with the selected cross-linking agent is selected as the functional group.

It is preferable that at least one functional group and at least one cross-linking agent are selected respectively from the aforementioned preferable functional groups and from preferable cross-linking agents in such a manner as to be a combination to cause a cross-linking reaction with each other.

In the first structure, a particularly preferable functional group is —COOR (R is a substituted or unsubstituted hydrocarbon group). It is comparatively easy to introduce carboxyl groups into the carbon nanotubes, and the obtained substance (a carbon nanotube carboxylic acid) has excellent reactivity, so that it is comparatively easy to esterificate the functional group into —COOR (R is a substituted or unsubstituted hydrocarbon group). This functional group is susceptible to a cross-linking reaction and therefore is suitable for the formation of a coating film.

One of the cross-linking agents corresponding to the functional group is polyols. Polyols are hardened by a reaction with —COOR (R is a substituted or unsubstituted hydrocarbon group) to easily form a firm cross-linking member. Among polyols, glycerine and ethylene glycol not only have excellent reactivity with the functional group, but also have high biodegradability themselves, providing a small load to the environment.

In the first structure, the functional group of the cross-linked positions is —COOR (R is a substituted or unsubstituted hydrocarbon group). When ethylene glycol is used as the cross-linking agent, the cross-linked positions have the chemical structure —COO($CH_2$)$_2$OCO—, whereas when glycerine is used as the cross-linking agent, if two OH groups contribute to the cross-linking, the cross-linked positions have the chemical structure —COOCH$_2$CHOHCH$_2$OCO— or —COOCH$_2$CH(OCO—)CH$_2$OH, and if three OH groups contribute to the cross-linking, the cross-linked positions have the chemical structure —COOCH$_2$CH(OCO—)CH$_2$OCO—. The cross-linked positions can have any one of these four chemical structures.

On the other hand, the second structure is formed by chemically bonding the functional groups of plural carbon nanotubes. The reaction causing this chemical bonding is preferably any of dehydration condensation, substitution reaction, addition reaction, and oxidation reaction.

The cross-linked carbon nanotube structure with the second structure is a network structure composed of the cross-linked positions formed by chemically bonding the functional groups with each other which are bonded with the carbon nanotubes. Therefore, the sizes of the cross-linked positions for bonding the carbon nanotubes are fixed, depending on the functional groups to be bonded. Since the carbon nanotubes have an extremely stable chemical structure, functional groups other than the functional groups that are intended to be modified are unlikely to be bonded, and when these functional groups that are intended to be modified are chemically bonded with each other, the cross-linked positions can be structured as designed, thereby making the cross-linked carbon nanotube structure homogeneous.

Since the second structure is formed by chemical bonding between the functional groups, as compared with the case of cross-linking the functional groups by using a cross-linking agent, the lengths of the cross-linked positions between the carbon nanotubes can be reduced. This makes the cross-linked carbon nanotube structure dense, thereby facilitating to provide effects unique to the carbon nanotubes.

In the second structure, it is preferable to select, as the chemical bonding between the functional groups, one of —COOCO—, —O—, —NHCO—, —COO—, and —NCH— in a condensation reaction; to select one of —NH—, —S—, and —O— in a substitution reaction; to select —NHCOO— in an addition reaction; and to select —S—S— in an oxidation reaction.

Examples of the functional groups to be bonded with the carbon nanotubes before the reaction include: —OH, —COOH, —COOR (R is a substituted or unsubstituted hydrocarbon group), —X, —COX (X is a halogen atom), —SH, —CHO, —OSO$_2$CH$_3$, —OSO$_2$(C$_6$H$_4$)CH$_3$—NH$_2$, and —NCO. It is preferable to select at least one group from these.

Among these, —COOH is a particularly suitable functional group. It is comparatively easy to introduce carboxyl groups into the carbon nanotubes. Moreover, the obtained substance (a carbon nanotube carboxylic acid) has excellent reactivities, and can easily cause a condensation reaction by making use of a dehydration condensation agent such as N-ethyl-N'-(3-dimethylaminopropyl) carbodiimide, which is suitable for the formation of a coating film.

As described above, in the cross-linked carbon nanotube structure having the cross-linked positions with either the first structure or the second structure, plural carbon nanotubes form a network structure through plural cross-linked positions. Therefore, unlike the condition where carbon nanotubes are accidentally in contact with each other and substantially isolated from each other, excellent characteristics of the carbon nanotubes can be used in a stable manner.

Catalyst for Measurement

The catalyst for measurement is preferably composed of fine particles or small pieces. Since diminishing the catalyst for measurement functioning as the electrode part can improve the detecting sensitivity as mentioned above, it is preferable that the catalyst for measurement has an average diameter of 1 nm to 100 μm, more preferably 1 nm to 10 μm, and further preferably 1 nm to 1 μm.

Examples of the catalyst include: metals, metal oxides, proteins, and carbon pieces supporting these. The metals include: platinum, silver, gold, iron, copper, and silicon. The metal oxides include: platinum black, enzymes, iron oxide, cobalt oxide, titanium oxide, tin oxide, indium oxide, gallium oxide, silicon oxide, silicon, zinc oxide, ruthenium oxide, hafnium oxide, and tungsten oxide. The proteins include enzymes. These substances can be used alone or by combining two or more kinds, and it is possible to select any that can have a chemical reaction with the substance that is expected to be detected.

Insulator

As the material for the insulator, anything which can enclosed carbon nanotubes by being chemically bonded with them and which is a nonconductive material can be used, whether it is organic or inorganic. Here, the nonconductive material does not necessarily mean a perfect insulating material and can be a general semiconductive material. The insulator preferably has a volume resistivity value in a range of $1 \times 10^5$ to $1 \times 10^{10}$ Ωcm.

Preferable materials for the insulator include: polyetherketone and polyketone. Above all, aliphatic polyetherketone is preferable, and aliphatic polyetherketone having the structure represented by the Formula (1) shown below as a component is preferable as the basic skeleton. The aliphatic polyether ketone is a polymer containing no aromatic tube. Aliphatic polyether ketone contains a ketone group functioning to harden a polymer and an ether bond functioning to soften the polymer, so that controlling their numbers enables the control of the polymer's dynamic properties such as hardness while keeping the thermal stability, making a useful material as the insulator of an electrode.

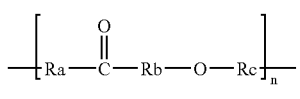

Formula (1)

In the Formula (1), each of Ra and Rb independently represents a substituted or unsubstituted divalent aliphatic hydrocarbon group; Rc represents a substituted or unsubstituted divalent aliphatic hydrocarbon group having an ether bond at a terminal thereof or a single bond; and n is an integer from 2 to 10000. It is possible to form a block copolymer with another polymer.

The aforementioned divalent aliphatic hydrocarbon group can be an aliphatic hydrocarbon group having 1 to 20 carbons, and can be any aliphatic hydrocarbon group of either straight chain, branched, or cyclic; however, a straight-chain aliphatic hydrocarbon group is preferable. One specific example is an alkyl chain having 1 to 20 carbons. Examples of the divalent aliphatic hydrocarbon group having an ether bond at a terminal thereof include the one with an ether bond (—O—) at the end of these aliphatic hydrocarbon groups.

Examples of the substituent which can be substituted by the aforementioned divalent aliphatic hydrocarbon groups include: —COOR, —COX, —Mgx, —X, —OR, —NR$^1$R$^2$, —NCO, —NCS, —COOH, —OH, —O, —NH$_2$, —SH, —SO$_3$H, —R'CHOH, —CHO, —CN, —COSH, —SR, and —SiR'$_3$ where X represents a halogen, and each of R, R$^1$, R$^2$, and R' represents a substituted or unsubstituted hydrocarbon group.

The Ra and Rb are substituted or unsubstituted divalent aliphatic hydrocarbon groups, and their specific examples include: —CH$_2$—, —CHNH$_2$—, —C(NH$_2$)$_2$—, —CHCN—, —C(CN)$_2$—, —CHOH—, —C(OH)$_2$—, —CO—, —CHSH—, —C(SH)$_2$—, —CHCOOH—, —C(COOH)$_2$—, —CHX—, and —CX$_2$—, and these can be repeated or combined. Here, X represents a halogen.

On the other hand, specific examples of Rc include: a single bond, and a substituted or unsubstituted divalent aliphatic hydrocarbon group which has an ether bond at a terminal thereof and which is represented by —Rc'—O—. Specific examples of Rc' include: —CH$_2$—, —CH$_2$—, —CHNH$_2$—, —C(NH$_2$)$_2$—, —CHCN—, —C(CN)$_2$—, —CHOH—, —C(OH)$_2$—, —CHSH—, —C(SH)$_2$—, —CHCOOH—, —C(COOH)$_2$—, —CHX—, and —CX$_2$—, and these can be repeated or combined. It is also possible to repeat —Rc'—O—, or to combine —Rc'—O— structures composed of different Rc's. Here, X represents a halogen.

As the structural unit represented by the Formula (1), for example, when glycerine is used as the polyhydric alcohol, polyether ketone having the structural unit represented by the Structural formula (2) below is obtained. In the Structural formula (2), n represents an integer from 2 to 10000.

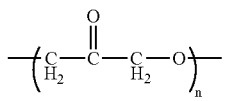

Structural formula (2)

When glycerine and ethylene glycol are used for the polyhydric alcohol as the raw material, polyetheretherketone having the structural unit represented by Structural formula (3) is obtained. In the Structural formula (3), m is an integer from 1 to 20, and n is an integer from 2 to 10000.

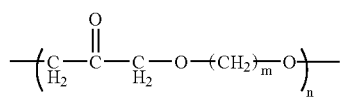

Structural formula (3)

Furthermore, as the structural unit represented by Formula (1), polyketones having the structural unit represented by the structural formulas below are exemplified. In the structural formulas below, each of m1, m2, and m3 is an integer from 1 to 20, and n represents an integer from 2 to 10000.

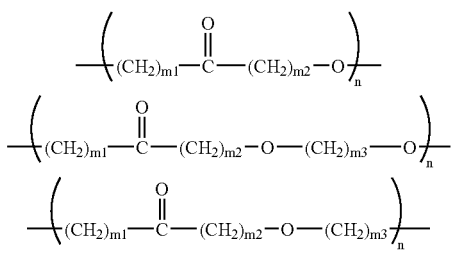

The aliphatic polyetherketone can be selected from the group consisting of —OH, —COOH, —COOR (R is a substituted or unsubstituted hydrocarbon group), —COX (X is a halogen atom), —NH$_2$, and NCO.

The aliphatic polyetherketone preferably has an average molecular weight of not less than 84 and not more than 1,000,000, and more preferably not less than 500 and not more than 500,000, and further preferably not less than 1,000 and not more than 100,000.

In the aliphatic polyetherketone, the ratio of the ether bonds to the ketone groups (the ether bonds/the ketone groups) is preferably 0.01 to 100, and more preferably 0.04 to 25.

As will be described later, in general, a ketone group improves the hardness of polymers, and an ether group improves the flexibility of polymers. Therefore, in a polymer, the number of ketone groups and the number of the ether groups can be adjusted to control the dynamic strength of the composite.

As will be described later, by using a polyhydric alcohol as a raw material, aliphatic polyetherketone having the structural unit represented by the Formula (1) in its chain can be synthesized. It is possible to synthesize a polymer composed by repeating the same structural unit, or to synthesize a polymer composed of structural units represented by the Formula (1) where Ra, Rb, and Rc are different.

It is also possible to synthesize a copolymer composed of the structural unit represented by the Formula (1) and another structural unit (not containing an aromatic group).

Specific examples of such a polymer include: a polymer composed of the structural unit represented by the Formula (1) and a polyether represented by the Formula (4), and a block copolymer containing these as components (a block copolymer composed of a polyetherketone part and a polyether part). One specific example is a block copolymer composed of polyetherketone composed of the structural unit represented by the Structural formula (2) and a polyether. In these polymers, in the Formulas (1) and (4), each of n, k, and l is an integer from 1 or larger; k is an integer from 1 to 20; n is an integer from 1 to 5000, and l is an integer from 1 to 5000. In the Formula (4), each of $R_1$ and $R_2$ is an H group or an alkyl group. It is possible that a part of the structural unit represented by the Formula (1) is substituted by the structure having residual OH groups (in the Formula (1), the ketone group is substituted by a COH group).

Formula (4)

The aliphatic polyetherketone can by synthesized so as to have a cross-linked structure. Having a cross-linked structure with a combination of a ketone group and an ether bond enables to obtain a composite stable both dynamically and thermally. For example there are cross-linked members formed by cross-linking the structural unit represented by the Formula (1) by glycerine or an aliphatic diol. Specific examples include cross-linked members in which, as shown in the structure below, the structural unit represented by the Structural formula (2) can be cross-linked by glycerine or an aliphatic diol compound.

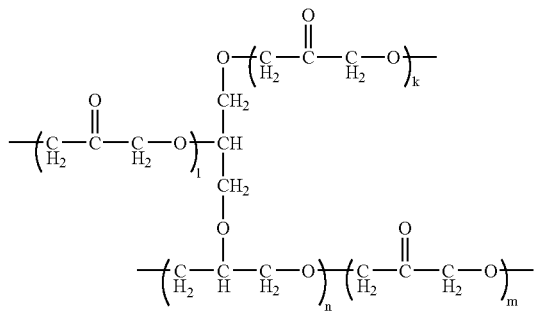

Method for Manufacturing an Electrode for Electrochemical Measurement

According to the method for manufacturing an electrode for electromechanical measurement of the invention, in the presence of a polymerization catalyst, as a raw material, a mixture solution of a polyhydric alcohol and carbon nanotubes having functional groups which have a polymerization reaction with the polyhydric alcohol is coated on the substrate after the substrate is covered with a conductor for current extraction so as to cause a polymerization reaction. In this polymerization reaction, polymerization is caused in the polyhydric alcohol and between the polyhydric alcohol and the functional groups of the carbon nanotubes, making it possible that the plural carbon nanotubes are chemically bonded with the polymer (insulator) and enclosed into the polymer (insulator) in a mutually electrically connected condition.

This manufacture method is suitable for industrial production because it enables the synthesis of a ketone group which improves the hardness of a polymer from a polyhydric alcohol, and particularly because it can produce polyetherketone which contains a ketone group and an ether group and which does not contain an aromatic group by using not petroleum but a polyhydric alcohol which can be handled easier than petroleum material due to its simple reaction process and minor load to the environment.

Here, examples of the functional group to have a polymerization reaction with a polyhydric alcohol modifying the carbon nanotubes include: —COOR, —COX, —NCO (R is a substituted or unsubstituted hydrocarbon group, and X represents a halogen atom). The use of —COOH (a carboxylic acid), which can modify carbon nanotubes comparatively easily, makes the polymerization dense, and achieves a more composite structure, that is, the carbon nanotubes are enclosed into the polymer (insulator) in tight contact, thereby obtaining high effects.

In the bonding positions where the plural carbon nanotubes and the polymer (insulator) molecules are bonded with each other, the functional group is, for example, —COOR (R is a substituted or unsubstituted hydrocarbon group). When glycerine is used as the polymer material, if two OH groups contribute to the chemical bonding with the carbon nanotubes, the bonding positions have the chemical structure —COOCH$_2$CHOHCH$_2$OCO— or —COOCH$_2$CH(OCO—)CH$_2$OH, and if three OH groups contribute to the chemical bonding with the carbon nanotubes, the bonding positions have the chemical structure —COOCH$_2$CH(OCO—)CH$_2$OCO—. The cross-linked positions can have any one of these two chemical structures.

On the other hand, when a catalyst for measurement is used, the electric connection between the carbon nanotubes and the catalyst for measurement can be established by two methods. A first method is to mix the catalyst for measurement into the carbon nanotube dispersant solution, to stir the mixture well in a mortar or a ball mill, and then to coat it to form an electrode. The second method is as follows. First, the carbon nanotubes are dispersed in a solution containing an insulator material, and the solution is coated after the conductor for current extraction is covered, and the solvent is evaporated. Next, one end of the obtained structure is cut so as to expose the carbon nanotubes. Then, the catalyst for measurement on the electrode surface thus prepared can be plated by electrolytic plating or the like so as to secure the connection of the catalyst for measurement with the surface of the exposed carbon nanotubes.

In the method for manufacturing the electrode for electrochemical measurement of the invention, a polymerization reaction involving an oxidation reaction can produce aliphatic polyketone, and a polymerization reaction involving a dehydration reaction can produce aliphatic polyetherketone. To be more specific, as the polymerization catalyst, an oxidation catalyst is used when polyketone is produced from a polyhydric alcohol, and a dehydration oxidation catalyst is used when polyetherketone is produced.

In producing polyetherketone, when polyether polyol is used as the polyhydric alcohol, either an oxidation catalyst or a dehydration oxidation catalyst can be used. Here, the oxidation catalyst represents a catalyst which oxidizes secondary hydroxyls and causes dehydration condensation between hydroxyl groups. The polymerization catalyst can be either liquid or solid; however, an aqueous solution can improve the mixing with a polyhydric alcohol, causing a catalyst action in a preferable manner. Preferable polymerization catalysts are those which can be partly or completely removed from the polymer in a volatile or nonvolatile polymerization catalyst at temperatures lower than the pyrolysis temperature of the polymer.

The polymerization catalyst is preferably at least one selected from sulfuric acid, nitric acid, hydrogen peroxide, Na$_2$Cr$_2$O$_7$, CrO$_3$Cl, and NaOCl, and it is particularly preferable to use sulfuric acid because of its susceptibility to the dehydration reaction and oxidization reaction, inexpensiveness and easiness to handle.

The amount of the polymerization catalyst (amount to be added) is preferably 0.1 to 100 mg per 1 g of material, and more preferably 0.5 to 80 mg, and further preferably 5 to 50 mg. Too little polymerization catalyst makes it difficult to have a polymerization reaction, while too much polymerization catalyst may cause foaming of the obtained polymer (insulator).

The polyhydric alcohol as the raw material is preferably a polyhydric alcohol containing a secondary alcohol and a primary alcohol in one molecule, and examples of such a polyhydric alcohol include: glycerine, 1,3,5-Trihydroxypentane, and 1,2,4-Trihydroxybutane, 1,2,6-Trihydroxyhexane. Above all, glycerine is preferable because of its inexpensiveness, small load to the environment, and susceptibility to polymerization reactions using dehydration and oxidization reaction catalysts.

In a polyetherketone, in general, a ketone group improves the hardness of a polymer, and an ether group improves the flexibility of the polymer. Therefore, the numbers of the respective groups can be adjusted to control the polymer's dynamic properties such as hardness. In other words, increasing the proportion of the ether bonds in the polymer improves the flexibility of the polymer, while increasing the proportion of the ether groups increases the hardness of the polymer.

However, according to the method of the invention, ketone groups are generated from a polyhydric alcohol which is the raw material. When a mixture of a polyhydric alcohol and a diol compound (for example, ethylene glycol) is used in polymerization, the diol compound can only generate ether bonds, so that the proportion of the ether bonds in the polymer molecules can be increased. Therefore, changing the mixture ratio of the polyhydric alcohol to the diol compound can control the flexibility of the polymer.

To be more specific, for example, when the polyhydric alcohol, glycerine, and diol compound are polymerized, if the polyhydric alcohol and the diol compound are polymerized alternately as shown in the following reaction formula, then polyetheretherketone can be obtained.

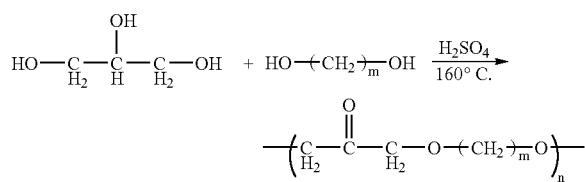

As a polyhydric alcohol, a block copolymer of polyetherketone and a polyether (a block copolymer of the structural unit represented by the Formula (1) described below and the structural unit represented by the formula 4 is formed from plural glycerine polymers and plural diol compounds.

In the method for manufacturing the electrode for electromechanical measurement of the invention, the polymerization reaction is preferably performed in such a manner as to have residual OH groups. The result is aliphatic polyetherketone having the structural unit represented by the formula (5) described later, or a water-soluble stable gel material.

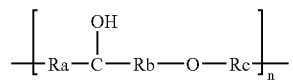

Formula (5)

To be more specific, for example, when nitric acid is used as the polymerization catalyst, since nitric acid has a boiling point of 120° C., the nitric acid as the polymerization catalyst can be vanished by heating at a temperature of 120° C. or higher before the raw material (for example, glycerine or a diol) is completely polymerized, thereby obtaining a gel polymer where some —OH groups are left without being synthesized into ketone groups.

Here, the gel material (polymer gel) is suitable for the formation of an electrode with a desired shape because the gel material has viscosity and hardly flows during coating or forming. It is possible to add sulfuric acid to the polymer gel, to coat or form the mixture, and heat it up to around 150° C. so as to manufacture a hardened polymer.

In order to cause a polymerization reaction, it is preferable to use the aforementioned polymerization catalyst and to heat it. The heating treatment can be done by any means; however, heating by electromagnetic waves is preferable because of its efficiency in generating a polymerization reaction.

The method for manufacturing the electrode for electrochemical measurement of the invention will be described in specific examples as the following reaction mechanism. The polymerization between the polyhydric alcohol and the functional groups of the carbon nanotubes is the same as described earlier. For example, when glycerine is used as the raw material and sulfuric acid is used as the dehydration catalyst, as shown in the reaction formula below, a dehydration condensation reaction between the primary alcohols, and an oxidation reaction of the secondary alcohol proceed. In the dehydration condensation reaction, $H_2O$ molecules are dissociated from the two primary alcohols in a glycerine molecule by the dehydration action of the sulfuric acid to form an ether bond. In an oxidation reaction, two hydrogen atoms are dissociated from H—C—OH which is a secondary alcohol to form a ketone group. The resulting product is aliphatic polyetherketone. In this case, unreacted OH groups can be present as mentioned above. It is also possible that the OH groups are chemically modified with molecules having functional groups which can react with the OH groups. It is also possible that the primary alcohol and the secondary alcohol have dehydration condensation between them, or the secondary alcohols have dehydration condensation between them.

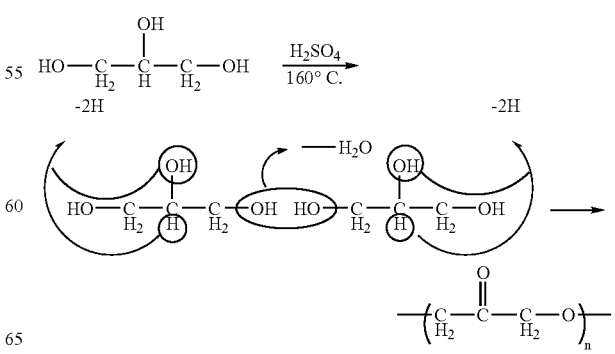

Thus, it is possible to manufacture the insulator into which the carbon nanotubes have been enclosed in such a manner as to be chemically bonded with the insulator.

The carbon nanotubes in the electrode prepared in the aforementioned methods are merely in contact with each other in the insulator, so that their contact condition is changed by bending or the like, thereby fluctuating the mechanical strength and electric properties, failing to fully exert the performance. Furthermore, to improve the electric conductivity requires increasing the amount of carbon nanotubes to be filled; however, this increase would cause a decrease in the amount of the insulating substance as the binder, thereby deteriorating the mechanical strength of the electrode itself.

Therefore, it is preferable to use the aforementioned cross-linked carbon nanotube structure. The cross-linked carbon nanotube structure can be formed by a cross-linking reaction besides the polymerization reaction with the polyhydric alcohol, or by a polymerization reaction between the previously formed cross-linked carbon nanotube structure and the polyhydric alcohol. When the previously formed cross-linked carbon nanotube structure is used as the raw material, the structure must have been modified with the functional groups which can have a polymerization reaction with the polyhydric alcohol.

The obtained electrode can be patterned into a pattern according to object. In this stage, the electrode structure itself is already stable, so that the patterning in this condition can provide a pattern according to object, without causing inconvenience such as scattering of the carbon nanotubes in the patterning process.

This patterning process has two types A and B as follows.

Type A comprises: applying dry etching to the electrode in the region other than the pattern according to object on the substrate surface so as to remove the electrode in the region, thereby patterning the electrode into a pattern according to object.

The operation of patterning the electrode into a pattern according to object can be divided into two processes: a mask forming process for providing a mask layer (preferably a resin layer such as a photoresist or a metal mask) onto the electrode in the region of the pattern according to object; and a removal process for removing the electrode exposed in the region other than the aforementioned region by applying dry etching (preferably applying the radicals of oxygen molecules. The radicals of the oxygen molecules can be generated by applying ultraviolet rays to oxygen molecules) to the side of the substrate where the electrode and the mask layer are formed. In that case, when the mask layer formed in the mask layer forming process is a resin layer such as the aforementioned photoresist, the removal process is followed by a resin layer exfoliating process for exfoliating the resin layer, so as to expose the patterned electrode.

In type A, the operation of patterning an electrode into a pattern according to object can be done by selectively applying gas molecule ions as ion beams to the electrode in the region other than the pattern according to object.

Type B comprises: a printing process for first preparing either a solution by dispersing carbon nanotubes into glycerine or the like and adding a dehydration catalyst such as sulfuric acid (hereinafter, carbon nanotube dispersant solution) or a gel by dispersing carbon nanotubes into the aforementioned gel polymer (composite) and adding a dehydration catalyst such as sulfuric acid (hereinafter, carbon nanotube dispersant gel), and then printing it into a pattern according to object; and a thermosetting process for thermosetting the carbon nanotube dispersant solution or a carbon nanotube dispersant gel.

Either type A or type B can be used for patterning.

The electrode for electrochemical measurement of the invention has been thus described by taking up preferable embodiments; however, the invention is not limited to these, and any of the conventionally well-known structures can be used by modifying it and/or be added as long as it has the structure of the invention.

EXAMPLES

The present invention will be described more specifically in the following examples; however, the invention is not limited to these examples.

Example 1

Carbon nanotubes modified with a carboxylic acid are synthesized as follows. 30 mg of multi-walled carbon nanotube (MWCNT) powder (purity: 90%, average diameter: 30 nm, average length: 3 μm, manufactured by Science Laboratory) is added to 20 ml of concentrated nitric acid (a 60%-by-weight aqueous solution, manufactured by Kanto Kagaku), and a flowing back is conducted for 20 hours at 120° C. so as to synthesize a carbon nanotube carboxylic acid. After the temperature of the solution is cooled down to room temperature, a 15-minute centrifugal separation is conducted at 5000 rpm so as to separate supernatant and sediment from each other. The collected sediment is dispersed in 10 ml of pure water, and again 15-minute centrifugal separation is conducted at 5000 rpm so as to separate supernatant and sediment (this is the completion of one cleaning operation). This cleaning operation is repeated five more times and then the sediment is collected in the end to obtain carbon nanotubes modified with a carboxylic acid.

0.02 g of the nanotubes modified with a carboxylic acid thus obtained is mixed with 1 ml of glycerine (manufactured by Kanto Kagaku), 0.2 g of platinum black (average diameter: 10 μm, manufactured by Wako Pure Chemical Industries, Ltd.) as a catalyst for measurement, and 10 μl of concentrated sulfuric acid (a 98%-by-weight aqueous solution, manufactured by Kanto Kagaku). 1 ml of this mixture solution is dropped on aluminum foil, and heated for 15 minutes at 190° C. When it is confirmed to have been hardened, the mixture solution is further heated for 30 minutes at 280° C. The result is an electrode in which carbon nanotubes and platinum black are dispersed. This electrode includes an electrical conduction part formed by the exposed parts of the carbon nanotubes and platinum black. Parts of the carbon nanotubes are in contact with the aluminum foil functioning as the conductor for current extraction. The volume resistivity value of the polyetherketone obtained from the glycerine alone is $1 \times 10^8$ Ωcm.

Figure 5:
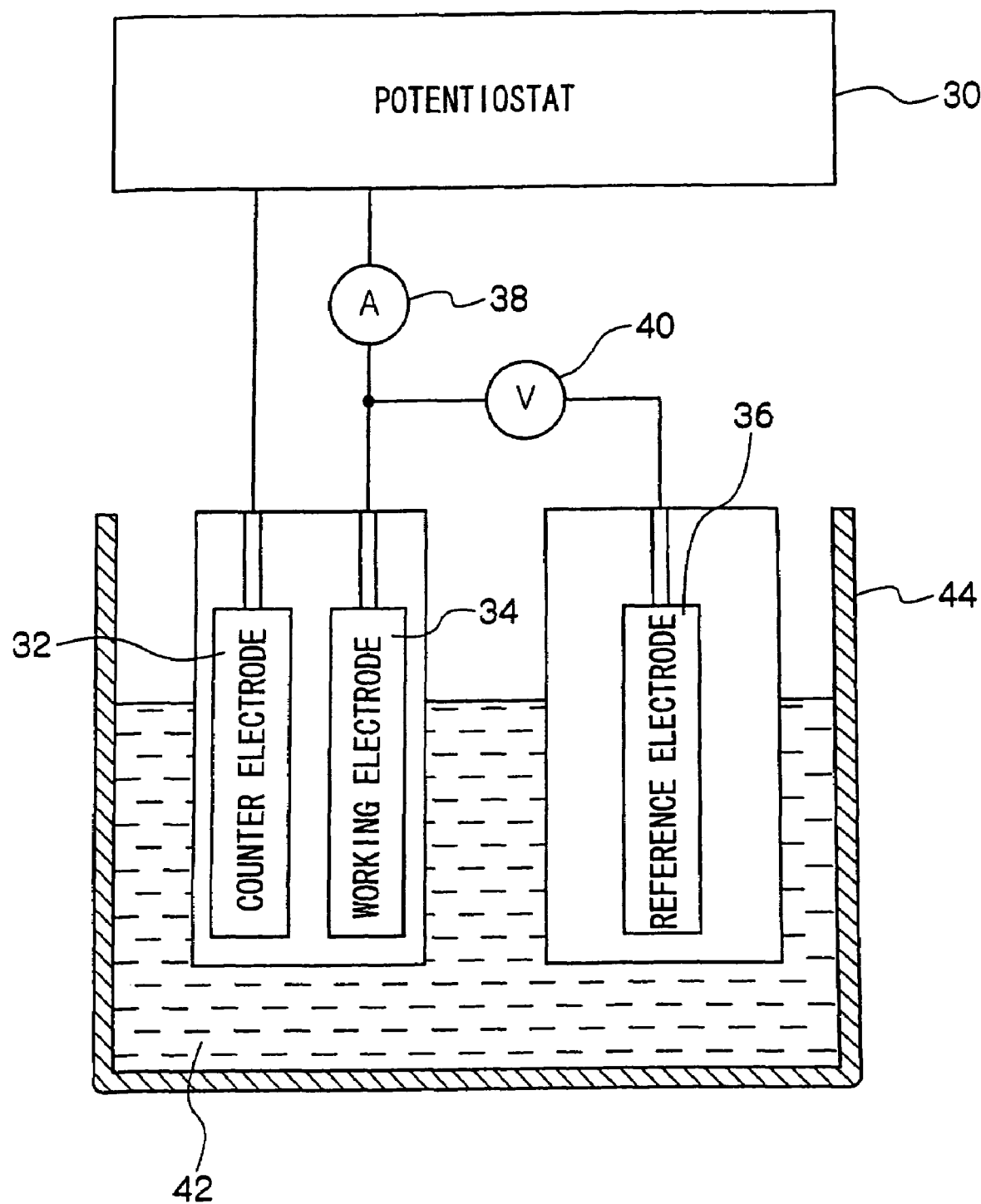
FIG. 5 is a simplified structural view showing the detecting device used in the examples.

The prepared electrode is placed on the detecting device having the structure shown in FIG. 5, and detection of hydrogen peroxide is conducted. The prepared electrode is cut into an arbitrary shape with scissors and arranged as a working electrode and a counter electrode. A Ag/AgCl electrode is further arranged as the reference electrode. As the electrolyte, 0.1 M of aqueous solution of potassium chloride (manufactured by Wako Pure Chemical Industries, Ltd.) is used. By using these electrodes, the cyclic voltammetries of the hydrogen peroxides whose concentrations have been adjusted to 0 pM, 1 pM ($=10^{-12}$ M), 10 pM, and 100 pM are measured. The measuring results are shown in FIG. 6.

Figure 6:
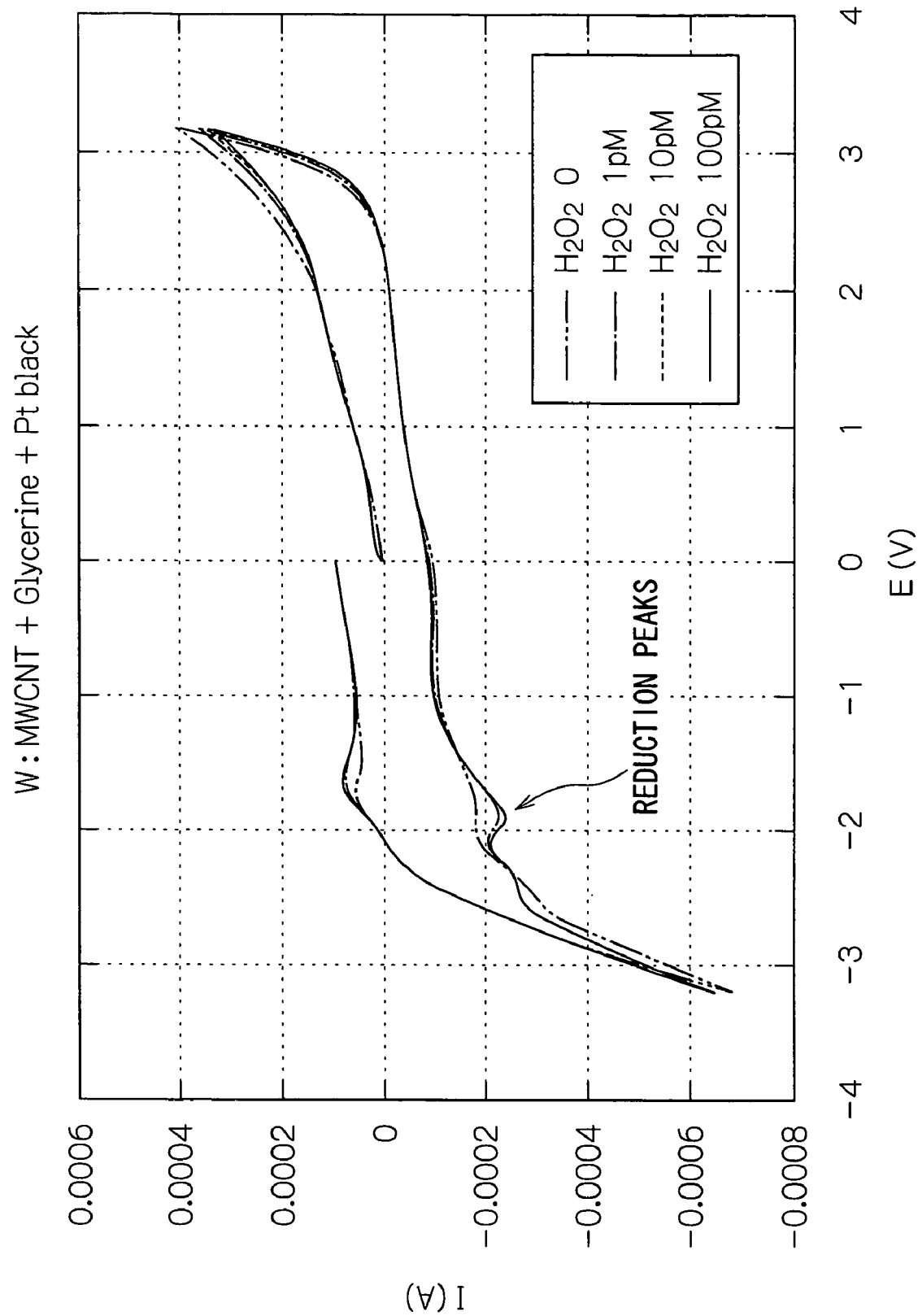
FIG. 6 is a cyclic voltammogram of hydrogen peroxides at the respective concentrations obtained in Example 1 described later.
Figure 7:
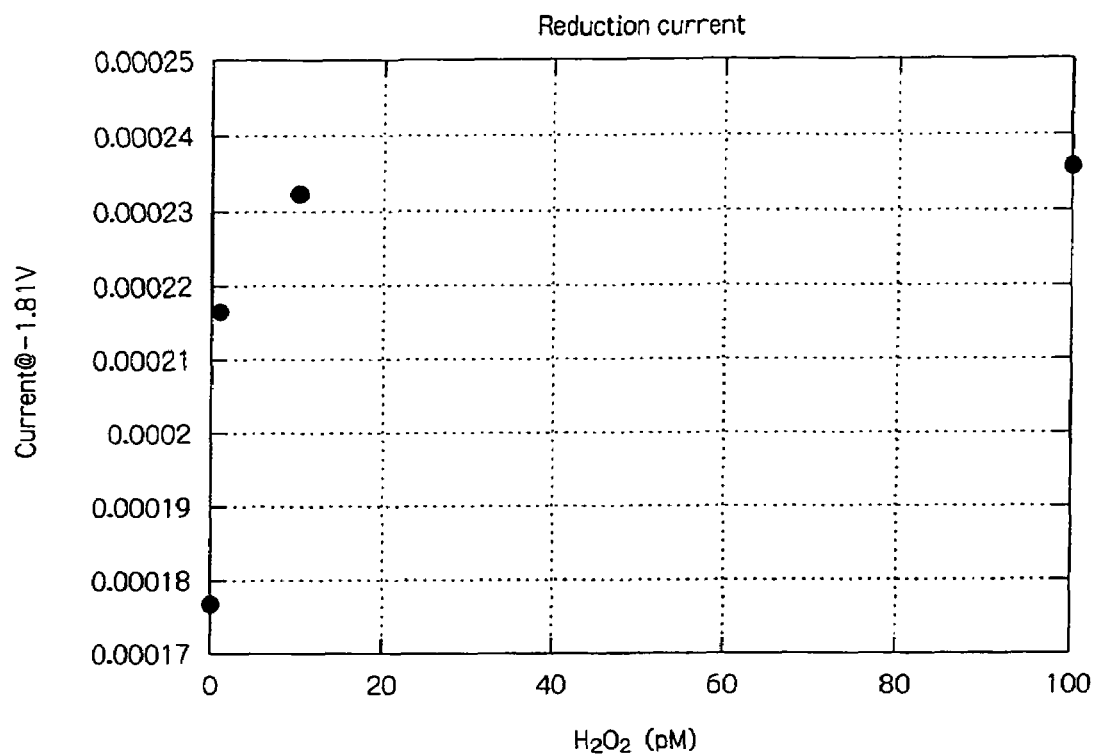
FIG. 7 is a view showing the relation between the current values and the concentrations of hydrogen peroxides at the reduction peaks obtained in Example 1 described later.

As known from FIG. 6, the reduction peaks of the hydrogen peroxides are observed around −1.8 V. The current values of the reduction peaks are plotted with respect to the concentrations of the hydrogen peroxides to obtain FIG. 7. Thus it has turned out that hydrogen peroxide with a concentration of 1 pM is detectable. No electrolysis of solvent occurs even if potential is swept in a range of +3.2 V to −3.2 V, indicating that there is a wide potential window of 6.4 V or higher.

The detecting device shown in FIG. 5 comprises a potentiostat 30, a counter electrode 32 linked with the potentiostat 30, a working electrode 34, and a reference electrode 36. The working electrode 34 is linked with the potentiostat 30 through an ammeter 38, and the working electrode 34 and the reference electrode 36 are linked with each other through a voltmeter 40. In the drawing, the reference numeral 42 represents an electrolytic aqueous solution of hydrogen peroxide, and the reference numeral 44 represents a container.

Example 2

Figure 8:
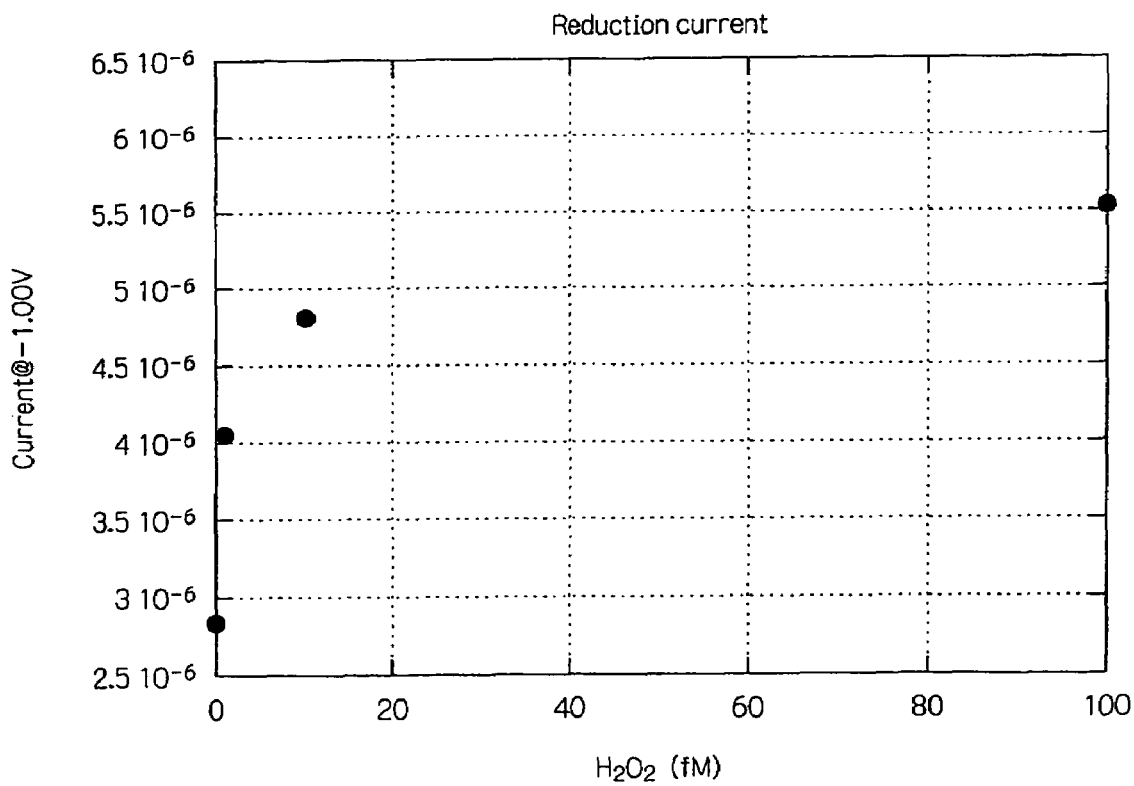
FIG. 8 is a view showing the relation between the current values and the concentrations of hydrogen peroxides at the reduction peaks obtained in Example 2 described later.

In the same manner as in Example 1, the cyclic voltammetries of the hydrogen peroxides whose concentrations have been adjusted to 0 fM, 1 fM ($=10^{-15}$ M), 10 fM, and 100 fM are measured. The current values at the reduction peaks of the hydrogen peroxides are plotted with respect to the respective concentrations, and the results are shown in FIG. 8. The results show that hydrogen peroxides up to 1 fM are detectable. Example 3 (the case that the platinum black is connected with the carbon nanotubes by electrolytic plating)

An electrode with carbon nanotubes exposed from the insulator film made of polyetherketone is obtained in the same manner as in Example 1 except that platinum black as the catalyst for measurement has not been mixed. Then, 1 g of platonic chloride hexahydrate (Wako Pure Chemical Industries, Ltd.) and 10 mg of lead acetate (Wako Pure Chemical Industries, Ltd.) are dissolved in 100 ml of water so as to prepare a plating solution. The previously prepared electrode and the platinum electrode as the counter electrode are soaked in this plating solution, and an electric current is passed through the solution at 4V for 5 minutes so as to plate the carbon nanotubes exposed on the electrode surface with platinum black by electrolysis plating, thereby obtaining the electrode of the invention. The cyclic voltammetries of the hydrogen peroxides whose concentrations have been adjusted to 0 pM, 1 pM ($=10^{-12}$ M), 10 pM, and 100 pM are measured to obtain the same results as in Example 1.

Comparative Example 1

20 mg of multi-walled carbon nanotubes (MWCNT) powder (purity: 90%, average diameter: 30 nm, average length: 3 μm, manufactured by Science Laboratory) and 1 g of polycarbonate (manufactured by Aldrich) as the insulator material are added to 5 ml of ethyl acetate as the solvent, and stirred well in a mortar. This mixture solution is applied on a slide, the solvent is evaporated, and wire as the conductor for current extraction is bonded with a conductive epoxy resin so as to obtain an electrode. In this case, however, the carbon nanotubes coagulate and form plumps of several hundred microns or larger in the insulator, failing to form a condition where micro electrodes are exposed from the insulator in massive parallel, which is one of the features of the invention.

What is claimed is:

1. An electrode for electrochemical measurement comprising a carbon nanotube and an insulator that encloses carbon nanotube, wherein:
   the carbon nanotube is enclosed by being chemically bonded with the insulator;
   part of the carbon nanotube forms an electrical conduction part exposed at a surface of the insulator; and
   a material of the insulator is an aliphatic polyetherketone containing a structural unit represented by the following Formula (1) as a component:

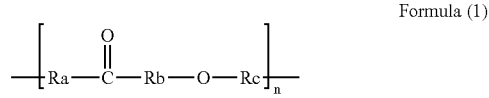

Formula (1)

wherein each of Ra and Rb independently represents a substituted or unsubstituted divalent aliphatic hydrocarbon group; Rc represents a substituted or unsubstituted divalent aliphatic hydrocarbon group having an ether bond at a terminal thereof or a single bond; and n is an integer from 2 to 10000.

2. An electrode for electrochemical measurement according to claim 1, wherein:
   the carbon nanotube comprises plural carbon nanotubes;
   the plural carbon nanotubes are electrically connected with each other; and
   the electrical conduction part is part of the plural carbon nanotubes exposed in plural spots on a surface of the insulator through the insulator.

3. An electrode for electrochemical measurement according to claim 1, wherein:
   the carbon nanotube comprises plural carbon nanotubes; and
   the plural carbon nanotubes form a network structure by being electrically connected with each other by chemical bonding.

4. An electrode for electrochemical measurement according claim 1, wherein in the structural unit represented by the Formula (1), Ra and Rb represent $CH_2$, and Rc represents a single bond.

5. An electrode for electrochemical measurement according claim 1, wherein in the structural unit represented by the Formula (1), Ra and Rb represent $CH_2$, and Rc represents $-(CH_2)_m-O-$ in which m is an integer from 1 to 20.

6. An electrode for electrochemical measurement according to claim 1, wherein the insulator has a volume resistivity value in a range of $1\times10^5$ to $1\times10^{10}$ Ωcm.

* * * * *